United States Patent
Gizurarson et al.

(10) Patent No.: US 11,337,949 B2
(45) Date of Patent: May 24, 2022

(54) THERMOSTABLE FORMULATION OF BIOLOGICALLY ACTIVE SUBSTANCES

(71) Applicant: CAPRETTO EHF., Grenivík (IS)

(72) Inventors: Sveinbjorn Gizurarson, Reykjavik (IS); Helga Helgadottir, Akranes (IS); Thordis Kristmundsdottir, Seltjarnarnes (IS)

(73) Assignee: CAPRETTO EHF., Grenivík (IS)

( * ) Notice: Subject to any disclaimer, the term of this patent is extended or adjusted under 35 U.S.C. 154(b) by 0 days.

(21) Appl. No.: 16/311,776

(22) PCT Filed: Jun. 19, 2017

(86) PCT No.: PCT/IS2017/050009
§ 371 (c)(1),
(2) Date: Dec. 20, 2018

(87) PCT Pub. No.: WO2017/221275
PCT Pub. Date: Dec. 28, 2017

(65) Prior Publication Data
US 2019/0209511 A1    Jul. 11, 2019

(30) Foreign Application Priority Data
Jun. 20, 2016 (IS) .......................... 050153

(51) Int. Cl.
A61K 31/23 (2006.01)
A61K 9/00 (2006.01)
A61K 9/08 (2006.01)
A61K 47/10 (2017.01)
A61P 31/00 (2006.01)

(52) U.S. Cl.
CPC .............. *A61K 31/23* (2013.01); *A61K 9/006* (2013.01); *A61K 9/0014* (2013.01); *A61K 9/0031* (2013.01); *A61K 9/0034* (2013.01); *A61K 9/0043* (2013.01); *A61K 9/0046* (2013.01); *A61K 9/0048* (2013.01); *A61K 9/08* (2013.01); *A61K 47/10* (2013.01); *A61P 31/00* (2018.01); *Y02A 50/30* (2018.01)

(58) Field of Classification Search
CPC .. A61K 2300/00; A61K 31/23; A61K 31/231; A61K 47/10; A61K 8/375; A61K 8/86; A61K 9/0014; A61K 9/0031; A61K 9/0034; A61K 9/0043; A61K 9/0046; A61K 9/0048; A61K 9/006; A61K 9/08; A61P 31/00; A61Q 11/00; A61Q 17/005; Y02A 50/30; Y02A 50/473
See application file for complete search history.

(56) References Cited

U.S. PATENT DOCUMENTS

| | | |
|---|---|---|
| 2005/0043402 A1 | 2/2005 | Thormar et al. |
| 2005/0058673 A1* | 3/2005 | Scholz .................... A61P 31/10 424/401 |
| 2008/0275030 A1* | 11/2008 | Gizurarson .......... A61K 9/0043 514/220 |
| 2011/0281918 A1 | 11/2011 | Bucher et al. |
| 2013/0143831 A1 | 6/2013 | Embil et al. |
| 2016/0158248 A1 | 6/2016 | Gizurarson |
| 2019/0209510 A1* | 7/2019 | Gizurarson ............. A61P 31/10 |

FOREIGN PATENT DOCUMENTS

| | | |
|---|---|---|
| EP | 0243145 A2 | 10/1987 |
| FR | 2827770 A1 | 1/2003 |
| WO | 2005/023233 A2 | 3/2005 |
| WO | 2014/121189 A1 | 8/2014 |
| WO | 2016/022170 A1 | 2/2016 |

OTHER PUBLICATIONS

Huang, Chifu B., et al. "Short- and medium-chain fatty acids exhibit antimicrobial activity for oral microorganisms." Archives of oral biology 56.7 (2011): 650-654.
Oh, Deog-Hwan, and Douglas L. Marshall. "Antimicrobial activity of ethanol, glycerol monolaurate or lactic acid against Listeria monocytogenes." International journal of food microbiology 20.4 (1993): 239-246.
Iceland Search Report for corresponding Application Serial No. EU050153, dated Nov. 29, 2016, pp. 1-2.
PCT International Search Report and Written Opinion for corresponding International Application Serial No. PCT/IS2017/050009, dated Sep. 12, 2017, pp. 1-14.

* cited by examiner

*Primary Examiner* — Kara R McMillian
(74) *Attorney, Agent, or Firm* — Tarolli, Sundheim, Covell & Tummino LLP

(57) ABSTRACT

A formulation to be used for administering a therapeutically effective amount of an antimicrobiologically active monoglyceride to a mammal including administering a pharmaceutical composition having a total volume of 1-5000 μL to a surface of the mammal such as the nasal, ocular, otal, pharynx, larynx, sinuses, oral cavity, vaginal or dermal surface, the pharmaceutical composition including the therapeutically effective amount of the antimicrobiologically active monoglyceride dissolved or suspended in a volume of 1-5000 μL of an methoxypolyethylene glycol referred to as mPEG and polyoxyethylene glycol (PEG)-fatty acid mono- or diglyceride so that upon administration of the pharmaceutical composition to the surface the formulation expresses thermostability within the range from below zero degrees C. to above 35-40° C. and thereby allows the antimicrobiologically active monoglyceride to exert its therapeutic effect.

17 Claims, No Drawings

THERMOSTABLE FORMULATION OF BIOLOGICALLY ACTIVE SUBSTANCES

RELATED APPLICATIONS

The present application is a U.S. National Stage application under 35 USC 371 of PCT Application Serial No. PCT/IS2017/050009, filed on 19 Jun. 2017; which claims priority from IS Patent Application No. 050153, filed 20 Jun. 2016, the entirety of both of which are incorporated herein by reference.

FIELD

This invention relates to novel formulations with microbicidal lipids that are stable and remain dissolved within a wide temperature range.

INTRODUCTION

The uses of antimicrobial substances are important to combat viral, fungal, prion or bacterial infections. This is particularly true in the field of ear infections where 1-2% of general practicioner's visits are due to external or middle ear infections, upper respiratory tract infections such as nasal, sinus, pharynx, larynx infections as well as dermatological infections, genitoureal infections etc., which are afflicted with viral, fungal or bacterial infections. Current practice uses antibiotics to fight systemic and topical infections with varying success.

Antibiotics are generally effective and regarded safe with few side effects. However, there is a risk of generating resistance. Antimicrobial lipids such as, but not limited to glycerol monocaprate, glycerol monocaprylate, glycerol monolaurate, glycerol dicaprin, glycerol dicaprylate, glycerol dilaurate, glycerol tricaprin, glycerol tricaprylate, glycerol trilaurate, octylglycerol, monomyristin, monopalmitolein, monoolein, propylene glycol monocaprate, propylene glycol monocaprylate, propylene glycol monolaurate, and combinations thereof, have shown to be highly effective against numerous microbes, both viruses, bacteria, prions and fungi. They are also known to avoid causing resistance, so these compounds are highly recommended for treating viral, prion, bacterial and/or fungal infections. These lipids or glycerides are natural compounds, found in human (and animal) breast milk. Therefore, this is the first antibacterial therapy an infant is exposed to after birth.

Numerous publications have shown the effect of these lipids on viruses, bacteria and fungi. A publication by Bergsson et al (APMIS 2001), Conley and Kabara (AAC 1973) and Isaacs et al (J. Nutr. Biochem. 1992) showed that monocaprin was bacteriocid for *Staphylococcus aureus, Staphylococcus epidermis, Streptococci A, Streptococci pyogenes, Haemophilus influenzae.*

Kabara et al. (AAC 1972) and Thorgeirsdottir et al. (Acta Odont. Scand. 2006) showed that monocaprin was effective against *Streptococcus D, Streptococcus mutans, Streptococcus pneumoniae, Corynebacteria* sp. *Nococardia asteroides, Micrococcus* sp. *Pseudomonas aeruginosa.*

Unpublished data from Sýni ehf (2012) and Bergsson et al. (1999) show that monocaprin is also effective against *Listeria monocytogenes* and *Lactobacillus jensenii.*

Bergsson et al (AAC 1998, AAC 1999, AAC 2001, Int. J. Antimicorb. Agents 2002) and Thormar et al (Appl. Environ. Microbiol. 2006) have shown that monocaprin is effective against *Chlamydia trachomatis, Neisseria gonorrhoeae, Helicobacter pylori, Campylobacter jejuni, Candida albicans* (yeast).

Kristmundsdottir et al. (J. Pharm. Sci. 1999), Isaacs et al. (J. Nutr. Biochem. 1992) and Hilmarsson et al. (APMIS 2005) have shown that monocaprin is effective against Herpes virus type 1 (HSV-1) and Herpes virus type 2 (HSV-2). Hilmarsson et al. (Arch Virol. 2007) has shown that monocaprin is effective against Respiratory syncytial virus (RSV) Influenza A virus and Parainfluenza virus type 2.

A large number of biologically active lipids such as glycerol monocaprate, glycerol monocaprylate, glycerol monolaurate, propylene glycol monocaprate, propylene glycol monocaprylate, glycerol dicaprin, glycerol dicaprylate, glycerol dilaurate, glycerol tricaprin, glycerol tricaprylate, glycerol trilaurate, octylglycerol, monomyristin, monopalmitolein, monoolein, propylene glycol monolaurate, and combinations thereof, have a limited degree of water-solubility and it is not possible to dissolve a clinically relevant amount in the relatively small volume which may be applied for the various clinical sites. Furthermore, in a dissolved state e.g. together with a surfactant such as but not limited to Tween 20 or Tween 80, these biologically active lipids tend to precipitate when the temperature goes below 10° C.

SUMMARY

The present invention relates to pharmaceutical compositions for local administration of a biologically active antimicrobial lipid to a mammalian surface such as the nasal mucosa, sinus mucosa, ocular mucosa, otal mucosa or the external ear, rectal mucosa, vaginal mucosa, uterus, buccal mucosa, pharynx, larynx mucosa, gingual mucosa, lung mucosa, GI mucosa and/or the skin. The formulations aer used for various antimicrobial lipids which remain in solution over a wide temperature range, including low temperatures such as about 4° C. and temperatures in the range 25-35° C., without precipitation or cloudiness forming.

For liquid or semiliquid compositions aimed to the nasal cavity, nasal mucosa, sinus cavity, sinus mucosa, ocular mucosa, otal mucosa or the external ear, rectal mucosa, vaginal mucosa, uterus, buccal mucosa, pharynx mucosa, larynx mucosa, gingual mucosa, lung mucosa, GI mucosa and/or the skin it is essential that an effective amount of the biologically active substance(s) can be dissolved in a volume of less than about 1000 μL, preferably in a volume of less than 300 μL and more preferably in a volume of less than 150 μL. A larger volume can be disagreeable to the patient and will evidently drain out or drain away. The result is that a part of the active substance is lost from the site. The volume for human adults is preferably from about 1 μL to about 1000 μL and more preferably from about 50 μL to about 150 μL to the administration site such as the nasal cavity. An exception is the vagina and/or the rectal route, where the volume may be as large as 5000 μL, preferably between 500-2000 μL.

Most surface regions, such as the mucosal epithelium are equipped with an important defense mechanism e.g. against inhaled dust, allergens and microorganisms. Therefore, the duration at the administration site is relatively short, such as about 15 minutes inside the nasal cavity due to the mucociliary clearance removing foreign particles and excess mucus toward the pharynx. For this reason it is preferred that the lipids stay longer at the administration site. Therefore, one important object of this invention is to keep the antimicrobial lipids at the administration site for enough time to induce antimicrobial effects, such as longer than 15-20 minutes inside the nasal cavity or other mucosal surfaces such as but not limited to sinus mucosa, otal mucosa, ocular mucosa, external ear, rectal mucosa vaginal mucosa, uterus mucosa, buccal mucosa, pharynx mucosa, larynx mucosa, gungual mucosa, lung mucosa, GI tract mucosa and/or the skin.

Preferred formulations and/or compositions according to the invention are liquid and/or micells and/or nanoemulsion, and may comprise but are not limited to formulations such as gel, ointment, cream, paste, formulation incorporated into capsules or tablets, liposomes etc. aimed at surfaces in general such as the nasal cavity, sinus cavities, oral cavity (buccal, sublingual, gingual etc.), rectal, vaginal, urethral, uterus, gastro-intestinal, ocular, otal, pulmonal and the skin. It is important that an effective amount of the biologically active lipid(s) can be dissolved in appropriate volume of the vehicle in a volume of less than 5 mL, preferably in less than about 1000 µL, more preferably in a volume of less than 300 µL and even more preferably in a volume of less than 150 µL.

A variety of vehicle systems e.g. for the nasal, sinus, pharynx, otal, ocular, vaginal, buccal and dermal delivery of biologically active substances has been developed. Up to date the literature has suggested formulations containing lactic acid and alcohol (Thormar and Hilmarsson in *Lipids* 150, 1-11, 2007) as well as surfactants, an enhancer and hydrophobic and/or hydrophilic components such as carbopols or various forms of cellulose (3M Innovative Properties Company; WO/2005/023233). However, according to the present invention, in order to keep the lipids at the mucosal surface, it is found beneficial to include in the formulation a bioadhesive agent such as methoxypolyethylene glycol (mPEG).

The primary object of the present invention is to provide a pharmaceutical formulation for application of biologically active lipid to a mammalian surface such as but not limited to a mucosal surface or skin, which composition is capable of keeping the formulation soluble within a practical temperature range, stable and active against varieties of antimicrobial pathogens, without causing unacceptable damage to the mammalian surface. This object is fulfilled with the formulations of the invention.

DETAILED DESCRIPTION OF THE INVENTION

Unless otherwise specified, percentages herein are weight percentages, based on the total weight of a "ready to use" or "as used" composition.

In a first aspect the invention provides a pharmaceutical formulation for antimicrobial treatment through application to skin or mucosa, the formulation comprising:
(a) an antimicrobiologically active lipid selected from the group consisting of glycerol monocaprate, glycerol monocaprylate, glycerol monolaurate, propylene glycol monocaprate, glycerol dicaprin, glycerol dicaprylate, glycerol dilaurate, glycerol tricaprin, glycerol tricaprylate, glycerol trilaurate, octylglycerol, monomyristin, monopalmitolein, monoolein, propylene glycol monocaprylate, propylene glycol monolaurate,
(b) one or more methoxypolyethylene glycol substance(s) represented by the formula I:

$$CH_3-(O-CH_2-CH_2)_n-H \qquad (I)$$

wherein n is an integer of 1 to 25, (c) polyoxyethylene-glyceride having the formula (II):

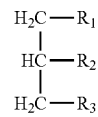

wherein R1, R2, and R3 are independently selected from the group consisting of $C_6$ to $C_{22}$ fatty acids ($-OCO-C_{5-21}H_{11-43}$), polyoxyethylene glycol (PEG) (($-O-CH_2-CH_2-)_n-H$) polymer and hydrogen, provided that it contains at least one $C_6$-$C_{22}$ fatty acid and at least one PEG group;
(d) optionally, a physiologically acceptable vehicle such as water, ethanol, polymers such as polyethyleneglycol or propylene glycol or combination thereof.

The active lipid ingredient is preferably at a concentration in the formulation within the range from about 0.01% such as from about 0.05% and more preferably from about 0.1%, such as from about 0.2%, such as from about 0.25%, to about 5%, such as to about 4%, such as to about 3%, such as to about 2%, such as to about 1%. The selected concentration may depend on the intended delivery form (solution, spray, gel, etc.) and intended location of application, as further described herein. In some embodiments the lipid substance is present in a concentration of about 0.1%, or about 0.2%, or about 0.25%, or about 0.3%, or about 0.4%, or about 0.5%, or about 0.6% or about 0.7% or about 0.8%, or about 0.9% or about 1.0%.

Preferably, the antimicrobial lipid component includes a monoester of a $C_8$-$C_{12}$ fatty acid(s), in position 1, having either S-isomer or R-isomer or combination thereof. Monoester having the fatty acid in position 2 is employed in some embodiments according to the invention and the lipid may additionally contain one or more component of diglycerides, triglycerides, pure glycerol and pure fatty acid.

As mentioned above, the pharmaceutical composition of the invention may comprise one or more biologically active lipid selected from the group consisting of but not limited to glycerol monocaprate, glycerol monocaprylate, glycerol monolaurate, propylene glycol monocaprate, propylene glycol monocaprylate, glycerol dicaprin, glycerol dicaprylate, glycerol dilaurate, glycerol tricaprin, glycerol tricaprylate, glycerol trilaurate, octylglycerol, monomyristin, monopalmitolein, monoolein, propylene glycol monolaurate, and combinations thereof and typically in a concentration as mentioned above, such as within the range of 0.01-5%, preferably within the range of 0.05-2%, more preferably in the range 0.1-1%.

In some preferred embodiments the active lipid ingredient comprises monocaprin, either alone or in combination with one or more further active lipid ingredient, selected from any of the herein mentioned lipid ingredients, such as but not limited to a combination of monocaprin an monolaurin. Other embodiments comprise monolaurin as sole active ingredient, or monolaurin in combination with another active lipid ingredient selected from those herein listed.

The methoxypolyethylene glycol substance is preferably present at a concentration within a range from about 0.1%, such as from about 0.2% such as from about 0.5%, more preferably from about 1%, to about 60%, such as to about 50%, such as to about 40%, such as to about 20%, such as to about 15%, such as to about 10%, such as to about 5%, such as to about 4%, or to about 3%, or to about 2%, such as but not limited to about 1%, about 1.5%, about 2%, about 2.5%, about 3%, or about 3.5%.

Methoxypolyethylene glycol as used herein refers generally to polyethylene glycol polymers, with a terminal methyl group. The term can be abbreviated as mPEG. As shown in Formula (I), the methoxypolyethylene glycol substance used in the present invention has polymer chain length with n being an integer in the range from 1 to 25, such as within a range from about 2, or from about 3, or from about 4, to about 25, such as to about 22, or to about 20, or to about 15, or to about 12, or to about 10. The mPEG may have a relatively uniform polymer length or a distribution of chains of different polymer length, within the given range. In some embodiments the distribution has a preferred average molecular weight, such as about 350, about 450, about 550 or about 650, corresponding to n being the average of about 7.2, about 9.5, about 11.7, and about 14, respectively. In one embodiment a combination product used in the formulation containing one or more substance(s) represented in the formula I is methoxypolyethylene glycol 350 (mPEG 350, such as Carbovax™ (DOW Chemical Company) and in another embodiment a combination used is the methoxypolyethylene glycol 550 (mPEG 550, e.g. Carbovax™). The numbers 350 and 550 refer respectively to average molecular weight of the respective substance.

Especially preferred for use in vehicle compositions according to the invention is Carbovax™ Sentry™ (mPEG 350 and mPEG 550) which refers to commercially available solvents of polymers of the above formula I, wherein n is mainly x and y, respectively, manufactured by The Dow Chemical Company mPEG 350 and mPEG 550 are colourless liquid miscible with water, alcohols, such as methanol, ethanol, n-proypanol, glycerol and various oils in all proportions and has a b.p. about 155° C. Both mPEG 350 and mPEG 550 are reported to be non-irritating when used in compositions for parenteral administration undiluted form as stated by Dow Chemicals.

The methoxypolyethylene glycols used in accordance with the present invention may e.g. be methoxy-diethyleneglyol (m2EG), methoxy-triethylene glycol (m3EG), methoxy-tetraethylene glycol (m4EG), methoxy-pentaethylene glycol (m5EG), methoxy-hexaethylene glycol (m6EG), methoxy-heptaethylene glycol (m7EG), methoxy-octaethylene glycol (m8EG), methoxy-nonaethylene glycol (m9EG), methoxy-decaethylene glycol (m10EG), methoxy-undecaethylene glycol (m11EG), methoxy-dodecaethylene glycol (m12EG), methoxy-tridecaethylene glycol (m13EG) and methoxy-tetradecaethylene glycol (m14EG). The ethylene glycols may be used in the form of the single compounds or a mixture of two or more methoxy-n-ethylene glycols, e.g. commercial products such as Carbovax™ Sentry™ (mPEG 350 or mPEG 550).

Methoxypolyethylene glycols are available in various qualities. Especially preferred are highly purified qualities such as Carbovax™ Sentry™ mPEG350 from The Dow Chemical Company.

The term polyoxyethylene-glyceride as used herein refers to a glyceride which is a mono- or diglyceride, i.e. with one or two fatty acid moieties connected to the glycerol backbone, and one or two polyoxyethylene glycol groups connected to one or both of the remaining one or two sites on the glycerol backbone of the glyceride. The set of substances referred to as polyoxyethylene-glyceride may also be referred to as polyoxyethylene glycol glycerides, polyoxyethylene mono- and diglycerides, or polyoxyethylene glycol mono- and diglycerides, PEG-glycerides or PEG mono- and diglycerides. Accordingly, the polyoxyethylene-glycerides used in the invention are suitably defined by Formula I and the definition provided above.

As mentioned above, the fatty acid component of the PEG-glyceride comprises $C_6$-$C_{22}$ fatty acid and preferably $C_6$-$C_{18}$ fatty acid, saturated or unsaturated, such as $C_6$-$C_{14}$ fatty acid, $C_8$ or $C_{10}$ fatty acid, or a combination thereof. Examples of $C_6$ to $C_{18}$ carboxylic acids, which are useful for the fatty acid R1, R2 or R3 component in formula (II) above are caproic, caprylic, capric, lauric, myristic, oleic, palmitic and stearic acid. Especially suitable for this invention are capric and caprylic acids, individually or together. In some embodiments a polyoxyethylene glycol glyceride is selected which is a combination product containing one or more substance(s) represented in the formula II being polyoxyethylene glycol (PEG)-fatty acid mono- or diglyceride such as macrogol-6-glycerol caprylocaprate, a mixture of mono and diesters made of polyoxyethyl glycerol ethers such as Softigen™ 767 from Cremer GmbH (Germany) or caprylocaproyl macrogol-8 glycerides, a mixture of mono-, di- and triglycerides and mono and di-fatty acid exters of polyethylene glycol such as Labrasol™ from Gattefosse (France).

The polyoxyethylene glycol (PEG or PEO) component used in the formation of the absorption promoter is, typically, a medium to high molecular weight material having a molecular weight of from about 200 to about 1200 such as, e.g., from about 300 to about 600. Suitable PEG-glycerides comprise in preferred embodiments a PEG component with a number of ethylene oxide units within the range from about 2, or from about 3, or from about 4, or from about 5 or from about 6, to about 30, such as to about 20, or to about 15, or to about 12, or to about 10, or to about 8, such as but not limited to having an average of about 5 ethylene oxide units, about 6 ethylene oxide units, about 7 ethylene oxide units, about 8 ethylene oxide units, or about 10 ethylene oxide units. For example, the above mentioned component magrogol-6-glycerol caprylocaprate is a mixture of mainly mono- and diesters of polyoxyethylene glycerol ethers mainly with caprylic (octanoic) and capric (decanoic) acids, with an average content of ethylene oxide being 6 units per molecule. Macrogol 6 glycerol caprylocaprate may be obtained by ethoxylation of glycerol and esterification with distilled coconut or palm kernel fatty acids, or by ethoxylation of mono- and diglycerides of caprylic and capric acids. Labrasol® is another example of a PEG-glyceride useful in the invention. Labrasol® is defined by the manufacturer as Caprylocaproyl macrogol-8 glycerides, with the fatty acid component being mainly caprylic (octanoic) and caproic (hexanoic) acid with the PEG component having an average of about 8 ethylene oxide units.

The PEG glycerol is preferably present at a concentration within a range from about 0.1%, such as from about 0.2%, such as from about 0.5%, more preferably from about 1%, such as from about 2%, such as from about 4% or from about 5%, to about 60%, such as to about 50%, such as to about 40%, such as to about 30% or to about 25%, such as to about 20%, such as to about 15% or to about 10%, such as but not limited to about 2%, about 5%, about 7.5%, about 10%, about 12%, about 15% or about 20%.

In accordance with a preferred aspect of the invention there is provided a pharmaceutical preparation comprising one or more methoxypolyethylene glycol and polyoxyethylene glycol (PEG)-fatty acid mono- or diglyceride in a formulation containing water and polymers such as polyethyleneglycol or propyleneglycol.

Preferably, the polymers are polyethylene glycols having an average molecular weight within a range from 200 about to 7500 or propylene glycol or mixtures thereof or single ethylene glycols such as tetraethylene glycol and pentaethylene glycol.

The polymer may in some embodiments be present in an amount within the range from about 0.5%, such as from about 1%, such as from about 1.5%, such as from about 2%, such as from about 3%, to about 15%, such as to about 12%, such as to about 10%, such as to about 8%, such as but not limited to about 7.5%, such as about 2%, about 3%, about 4% or about 5%.

It follows that water is present in many embodiments, typically within a range from about 50%, such as from about 60%, such as from about 65%, such as from 70%, such as from about 75%, to about 96%, such as to about 95%, such as to about 90%, such as to about 85%, such as but not limited to about 70%, about 75%, about 78%, about 80%, about 82% or about 85%.

The antimicrobial lipids in the formulations of the invention can be used to kill viruses such as but not limited to herpes virus type 1 and herpes virus type 2 (HSV-2), HIV, respiratory syncytial virus (RSV), influenza A virus and parainfluenza virus type 2, Adenoviruses, Coronavirus, Rhinovirus, Enterovirus, Human metapneumovirus, Varicella zoster virus, Zika virus; bacteria such as but not limited to *Staphylococcus aureus, Staphylococcus epidermis, Streptococci A, Streptococci pyogenes, Haemophilus influenzae, Streptococcus D, Streptococcus mutans, Streptococcus pneumoniae, Corynebacteria sp. Nococardia asteroides, Micrococcus sp. Pseudomonas aeruginosa, Listeria monocytogenes, Lactobacillus jensenii, Chlamydia trachomatis, Neisseria gonorrhoeae, Helicobacter pylori, Campylobacter jejuni, Mycobacterium tuberculosis, Moraxella catarrhalis, Veillonella parvula, Klebsiella species, Bordetella pertussis, Bordetella bronchiseptica, Corynebacterium diphtheria, Bacillus anthracis*; following fungi but not limited to *Candida albicans, C. albicans, C. tripicalis, C. parapsilosis, C. glabrata, C. parakrusei, C. guillermondi, C. dubliniensis, Trichophyton rubrum, Malassezia*; and prions such as but not limited to "mad cow" disease prion.

Of course, salts, metabolic precursors, derivatives and mixtures of these antibacterial lipids may also be used where desired.

Examples of infections to be treated or prevented by the formulation according to the invention may be any infection of the skin or mucosa caused by bacteria, virus or fungi towards which the microcidal lipids described herein are effective. Mucosa or mucosal membranes or surfaces may be the oral, aural, nasal, lung, gastro-intestinal, vaginal or rectal mucosa (as well as the surroundings) and the skin may be intact skin or skin which in some way have been injured. Examples of such fungi, bacteria and virus which can cause infection of the skin or mucosa are e.g. fungi such as e.g. Dermatophytes, Black piedra, White piedra, Tines nigra, and Tines versicolor; bacteria such as e.g. *Escherichia coli, Pseudomonas aerginosa*, and *Staphylooccus aureus*; virus such as e.g. influenza virus A, influenza virus B, influenza virus C, parainfluenza virus, mumps virus, Newcastle disease virus, viruses of rinderpest, canine distemper virus, respiratory syncytial virus, rabies virus, herpes simplex type 1, herpes simplex type 2, herpes genitalis, varicella zoster, cytomegalovirus, and Epstein-Barr virus.

It is also contemplated that the lipid is useful for the prevention or treatment of infection by a retrovirus such as e.g. human immuno deficiency Virus (HIV), sarcoma viruses, leukemia viruses, and human lymphotropic viruses types 1 and 2, and/or for the prevention or treatment of acquired immune deficiency syndrome (AIDS).

As has already been pointed out the active substance must be present in an effective amount within a total volume of less than 10 mL, preferably less than 1000 µL, for certain surfaces the total volume of less than 500 µL are preferable, or more preferably 50-150 µL.

The pharmaceutical preparation of the invention may furthermore comprise pharmaceutically acceptable excipients, appropriate for each delivery route or site.

Such excipient may be present in some embodiment in a concentration within a range from about 0.0001 to about 99%.

In some embodiments the pharmaceutical formulation additionally comprises one or more compound(s) selected from the group consisting of surfactant, absorption promoters, water absorbing polymers, microspheres, oils, emulsions, liposomes, substances that inhibit enzymatic degradation, alcohols, organic solvents, water, surfactants, hydrophobic agents, pH-controlling agents, preservatives and osmotic pressure controlling agents, cyclodextrines and propellants or mixtures thereof.

According to a preferred aspect of the invention such as but not limited to formulations vaginal or rectal delivery, the composition comprises less than 99% (w/w) of polyethylene glycol having an average molecular weight ranging from 200 to 7500.

The invention also relates to a formulation, according to the invention, where the vehicle optionally contains ethanol in a concentration within a range from about 0.1%, such as from about 0.2%, such as from about 0.25%, such as from about 0.3% such as from about 0.5%, to about 5%, such as to about 4%, such as to about 3%, such as to about 2.5%, such as but not limited to about 1%, or about 1.5%, about 1.75%, or about 2%, or about 2.25%, or about 2.5%, or about 3%.

Examples of suitable agents which are also spermicides that are included in the formulation in some embodiments of the invention are e.g. surfactants such as nonoxynol-9, chelating agents such as ethylenediaminetetraacetic acid (EDTA), channel-forming ionophores such as gramicidin, and other spermicidal agents such as benzalkonium chloride, sodium docusate and cholate acid and salts thereof.

The invention also relates to a method for treatment of animals such as pets: for example but not limited to dogs, cats, rabbits, guinea pigs, farm animals: such as but not limited to horses, sheep, pigs, cattle, chicken or captured wild animals with an effective amount of a biologically active lipid wherein the dosage unit quantity of a biologically active substance is applied to a surface of the animal to be treated in a formulation according to the invention. The volume administered to each animal, administration site, should preferably be calculated based on the relative human/animal surface area that need to be exposed.

The invention also relates to a method for treating industrial surfaces, walls, tables, floors, equipments, instruments or as an aerosol where bacteria, virus, fungi or prions may need to be eliminated, and formulations suitable for such purpose.

The mucosal membrane to which the pharmaceutical preparation of the invention is administered may be any mucosal membrane of the mammal to which the biologically active lipid is to be given, e.g. in the nose, sinuses, vagina, eye, ear, mouth, pharynx, genital tract, lungs, gastrointestinal tract, or rectum, preferably the mucosa of the nose, sinuses mouth (buccal, gingual, sublingual or to the hard palate), pharynx, larynx, vagina, uterus and the air. The pharmaceutical preparation may also be administered to the skin and/or the nails.

The pharmaceutical compositions of the invention may be administered in the form of a sublingual lozenge or troche or a buccal, pharynx, ear, sinus or nasal spray or drops in the form of a solution, micells, nanoemulsion, optionally in water and/or together with polymers such as polyethylene glycol or propylene glycol, optionally in the form of slightly viscous solution or as a solid or semisolids in the form of a suppository or vagitory.

Both the methoxypolyethylene glycol of the formula I and the polyoxyethylene glycol (PEG)-fatty acid mono- or diglyceride comprising of the formula II are considered to be a pharmaceutically acceptable carrier, especially a pharmaceutically acceptable carrier for mucosal and dermal (surface) administration.

According to another aspect of the invention methoxy-polyethylene glycols of the formula I are considered as a bioadhesive agent and the polyoxyethylene glycol (PEG)-fatty acid mono- or diglyceride comprising of the formula II is a thermostabilizing agent allowing the formulation to keep the lipids dissolved at temperatures below freezing point ($-10°$ C.) and up to $60°$ C. In some embodiments the lipids are maintained dissolved down to a temperature of about $-10°$ C., or to a temperature of about $-5°$ C., or to a temperature of about $-4°$ C., such as to about $-2°$ C., and preferably the lipid is dissolved in a temperature range from about $0°$ C., such as from about $4°$ C. up to about $50°$ C. and more preferably up to about $40°$ C.

The thermostabilizer, polyoxyethylene glycol (PEG)-fatty acid mono- or diglyceride can be the product of an esterification reaction between a polyoxyethylene glycol, glycerol and one or more straight chain $C_6$-$C_{22}$ carboxylic acids. Alternatively the component may be prepared by oligomerizing or polymerising ethylene oxide in the presence of an ester of glycerol and one or more of such $C_6$-$C_{22}$ carboxylic acids (glyceride esters). Still another route and the preferred one is by reacting a carboxylic acid glyceride ester or esters with a fully pre-formed polyoxyethylene glycerol under conditions to achieve alcoholysis. The term "carboxylic acid glyceride ester", is employed in this description in the conventional sense to mean an ester which has been derived from glycerol and a carboxylic acid.

Suitable PEG-glyceride for use in some embodiments of this invention, and which are commercially available, are Softigen™ 767, produced by Cremer GmbH (Witten, Germany) and Labrasol™, produced by Gattefosse Corp. (Paris, France). Softigen™ 767 contains following specifications: Value Acid value≤1 mg KOH/g Saponification value 90-100 mg KOH/g Iodine value <1 mg 1/100 mg Colour <150 APHA Freeze test Clear solution at $0°$ C. (24 h) Water content max. 0.5% (Carl Fisher test) Viscosity 150-175 mPa·s Refractive index 1.464-1.466. Labrasol™ contains following specifications: Acid value ≤2.00 mg KOH/g, Saponification value 85 to 105 mg KOH/g, Iodine value ≤2.00 gI2/100 g; Color (Gardner scale)≤2.5, Appearance as oily liquid at $20°$ C., Viscosity at $20°$ C. is 80 to 110 mPa·s and the Refractive Index at $20°$ C. is 1.450 to 1.470.

EP-0351651 describes the use of PEG-$C_8$/$C_{10}$-glycerides as an absorption promoter for insulin. Especially for orally and buccally administered insulin. From the disclosure it appears that an increase in concentration of PEG-$C_8$/$C_{10}$-glycerides results in an increase in absorption. With respect to a nasal composition the composition described has a relatively high concentration of absorption enhancer, namely about 50% w/w. WO2003070280 (Absorption enhancing agent) describes the use of PEG-$C_8$/$C_{10}$-glycerides as absorption promoter for e.g. sumatriptan, in most preferred concentrations of 0.1-10%. Here, the function of PEG-$C_8$/$C_{10}$-glycerides should not promote absorption, since that will remove the active ingredient from the surface such as the mucosal surface, and into the systemic circulation. However, PEG-$C_8$/$C_{10}$ is able to act as a thermostabilizer for formulations containing lipids that are insoluble in water. Lipids such as monocaprin will easily precipitate in aqueous formulations when exposed to temperature below $10°$ C. or above $25°$ C. Surprisingly, PEG-$C_8$/$C_{10}$-glycerides have shown to increase the thermostability of aqueous lipid solution to a temperature below zero or above $30$-$40°$ C.

The present invention makes use of the findings by the inventors that certain PEG-glycerides can be used as a thermostabilizer. It is especially interesting that the present inventors have observed that when such PEG-$C_8$/$C_{10}$-glycerides are replaced with polymers such as PEG or propylene glycol, this thermostabilizing effect is lost. The PEG-glyceride substance is fully water-soluble and produces a non-viscous solution together with water or saline. The substance together with mPEG of the present invention provides enhanced thermostability which is important when most mammalian surfaces have temperature above $25°$ C., and it keeps this formulation stable for a longer duration at the mammalian surface. Use of the invention provides the ability to achieve significant antimicrobial effects on mammalian surfaces infected with viruses, bacteria, fungi and/or prions due to increased stability of the formulation, without causing unacceptable irritation of the surface.

Normally, the PEG polymer comprises $PEG_{2-30}$ residues of polyoxyethylene, having in the range of 2-30 polyoxyethylene units, such as, e.g., a $PEG_{2-20}$ residue of polyoxyethylene having in the range of 2 to 20 polyethylene units, a $PEG_{3-10}$ residue of polyoxyethylene having in the range of 3 to 10 polyoxyethylene units or a $PEG_{3-6}$ residue of polyoxyethylene having in the range of 3 to 6 polyoxyethylene units.

In a composition according to the present invention for nasal administration, in one embodiment the concentration of component i) (mPEGs) in the composition is at the most 50% v/v such as, e.g., within a range from about 0.1% to about 15% v/v and component ii) (PEG-glycerides) in the composition is at the most 50% v/v such as, e.g. from about 0.1% to about 15% v/v. Alternatively, the concentration of component i) in the composition is at the most about 10% v/v and component ii) in the composition is at the most about 10% v/v.

The delivery system according to the invention can be optimized e.g. with respect to bioadhesion. For example mPEG 350, in same concentration as PEG200, has a surprisingly positive effect on the bioadhesion and the duration at the mammalian surface compared with lower molecular weight PEG 200. This is of importance where the formulation is used, to achieve enough time for the lipids to induce antimicrobial effects.

If desired, the pharmaceutical compositions of the present invention can optionally include additional compounds to enhance the solubility of the therapeutic agent. Examples of such compounds, include: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000 or tetrahydrofurfuryl alcohol PEG ether (glycofurol, available commercially from BASF under the trade name Tetraglycol);

amides, such as 2-pyrrolidone, 2-piperidone, .epsilon.-caprolactam, N-alkyl-pyrrolidone, N-hydroxyalkylpyrrolidone, N-alkylpiperidone, N-alkylcaprolactam, dimethylacetamide, and polyvinylpyrrolidone; esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, delta-valerolactone and isomers thereof, beta-butyrolactone and isomers thereof; and other solubilizers known in the art, such as dimethyl acetamide, dimethyl isosorbide (Arlasolve DMI (ICI)), N-methyl pyrrolidones (Pharmasolve (ISP)), monooctanoin, diethylene glycol monoethyl ether (available from Gattefosse under the trade name Transcutol), and water.

For the manufacturing of suppositories or vagitories or in case there is a need for additional fat, the formulation may additionally contain one or more of cocoa butter, high molecular weight polyethylene glycol, castor oil, paraffin oil, and adeps solidus.

Formulations of the invention further comprise in some embodiments solubilizer and such formulations are also within the scope of the invention. Except where indicated, suitable solubilizer compounds are readily available from standard commercial sources.

Preferred solubilizers in the formulation according to the invention include triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-1000, glycofurol, transcutol, propylene glycol, and dimethyl isosorbide. Particularly preferred solubilizers include sorbitol, glycerol, triacetin, ethyl alcohol, PEG-300-400, glycofurol and propylene glycol.

The amount of solubilizer that can be included in formulations of the present invention is not particularly limited. Of course, when such compositions are ultimately administered to a patient, the amount of a given solubilizer is limited to a bioacceptable amount, which is readily determined by one skilled in the art. In some circumstances, it may be advantageous to include amounts of solubilizers far in excess of bioacceptable amounts, for example, to maximize the concentration of therapeutic agent, with excess solubilizer removed prior to providing the composition to a patient using conventional techniques, such as distillation or evaporation. Typically, the solubilizer will be present in an amount within a range from about 1% to about 100%, more typically within a range from about 5% to about 75% by weight or within a range from about 5% to about 25% by weight.

Other excipients that may be comprised in the formulation of the invention include but are not limited to the following: pH-controlling agents, such as, nitric acid, phosphoric acid, or acetic acid, citrate: Preservatives and osmotic pressure controlling agents, such as glycerol, sodium chloride, methyl paraoxybenzoate, or benzoic acid; Powder compositions, such as, alfa-, beta- and gamma-cyclodextrines, cellulose and derivatives; Microspheres, nanospheres, virosomes, proteosomes, liposomes and emulsions compositions, such as, starch, albumin, gelatine, or lecithins or lysoleciythins; Microencapsulated formulations; Propellants such as butane; Water.

The invention is explained more in detail with reference to the Examples which are to be considered only as illustrating the invention and not to be construed so as to limit the scope of the invention as set forth in the appended claims.

EXAMPLES

The following examples are provided to illustrate specific working embodiments of the invention without limiting its scope.

Example 1

Formulations were made to be used as nasal spray or ear drops to prevent and/or fight infections in the nose, the sinuses, ear canals, external ear etc. according to following:

| | Formulation | | | |
|---|---|---|---|---|
| Component | I | II | III | IV |
| Monocaprin | 0.5% | 0.5% | 0.5% | 0.5% |
| mPEG* | 2% | 2% | — | 2% |
| Propylene glycol | 4% | 4% | 4% | 4% |
| Labrasol ™ | 10% | — | 10% | 10% |
| Ethanol | — | — | — | 2% |
| Polysorbate 80 | 0.8% | 0.8% | 0.8% | 0.8% |
| Water | 82.7% | 92.7% | 84.7% | 80.7% |

*Methoxypolyethylene glycol 350

Here the mPEG (in formulations I, II and IV), propylene glycol, polysorbate 80, ethanol (formulation IV) and Labrasol (formulation I and III) are mixed together whereafter monocaprin is dissolved in this mixture using vortex, ultrasound, heat and/or other standard methods. Then water is added to the mixture and gently mixed together using standard methods to receive a homogenious transparent solution.

These formulations I, II, III and IV were stored at average room temperature, at 4° C. and at 35° C. Formulations I and IV were able to pass all temperatures. Formulation II, however, precipitated at 4° C. and formulation III became clouded at 35° C. Formulations I and IV were the only one that were able to stay stable at all test-temperatures.

Example 2

Formulations were made that can be used as mouth spray, to prevent and/or fight infections in the pharynx, larynx, oral cavity or the tonsils. The components in the formulation consisted of the same ingredients as Formulations I, II, III and IV in Example I and IV here above, except that 0.1% mentholum is added Here the formulations were allowed to stay in temperature circulation, ranging from 0° C. up to average room temperature, for a few days. Formulation I and IV were the only formulations that were able to tolerate temperature cycles without precipitate or becoming cloudy.

Example 3

Formulations were made to be used as nasal spray or ear drops to prevent and/or fight infections in the nose, the sinuses, ear canals, external ear etc. according to following:

| | Formulation | | | |
|---|---|---|---|---|
| Component | I | II | III | IV |
| Monocaprin | 0.5% | 0.5% | 0.5% | 0.5% |
| Monolaurin | 0.5% | 0.5% | 0.5% | 0.5% |
| mPEG* | 2% | 2% | — | 2% |

-continued

| Component | Formulation | | | |
|---|---|---|---|---|
| | I | II | III | IV |
| Propylene glycol | 4% | 4% | 4% | 4% |
| Softigen ™ 767 | 10% | — | 10% | 10% |
| Ethanol | — | — | — | 2% |
| Polysorbate 80 | 0.8% | 0.8% | 0.8% | 0.8% |
| Water | 82.2% | 92.2% | 84.2% | 80.2% |

*Methoxypolyethylene glycol 350

Here the mPEG (formulation I, II and IV), propylene glycol, polysorbate 80, ethanol (formulation IV) and Softigen™ 767 (formulation I and III) are mixed together whereafter monocaprin and monolaurin (formulation I, II and III) are dissolved in this mixture using vortex, ultrasound, heat and/or other standard methods. Then water is added to the mixture and gently mixed together using standard methods to receive a homogeneous transparent solution.

These formulations I, II, III and IV were stored at average room temperature, at 4° C. and at 35° C. Formulations I and IV were able to pass solubility/cloudiness test at all measured temperatures. Formulation II, however, precipitated at 4° C. and formulation III became clouded at 35° C. Formulations I and IV were the only ones that were able to stay stable at all test-temperatures.

Example 4

Formulation was made that can be used as a nasal spray and eardrops, to prevent and/or fight infections in nose, sinuses, ear canals, external ear etc. Here the formulation was manufactured as prescribed in Example 1, formulation I, except that the formulation was made more viscous using 6% of glycerol and the concentration of polysorbate 80 was increased to 1%. The glycerol and the increase in the amount of polysorbate 80 did not affect the thermostability of the formulation.

Example 5

Formulations were made to be used as nasal spray or ear drops to prevent and/or fight infections in the nose, the sinuses, ear canals, external ear etc. according to following:

| Component | Formulation | | | |
|---|---|---|---|---|
| | I | II | III | IV |
| Monolaurin | 0.5% | 0.5% | 0.5% | 0.5% |
| mPEG* | 2% | 2% | — | 2% |
| Propylene glycol | 4% | 4% | 4% | 4% |
| Labrasol ™ | 10% | — | 10% | 10% |
| Ethanol | — | — | — | 2% |
| Polysorbate 80 | 0.8% | 0.8% | 0.8% | 0.8% |
| Water | 82.7% | 92.7% | 84.7% | 80.7% |

*Methoxypolyethyelene glycol 350

Here the mPEG (formulation I, II and IV), propylene glycol, polysorbate 80, ethanol (formulation IV) and Labrasol™ (formulation I and III) are mixed together whereafter monolaurin is dissolved in this mixture using vortex, ultrasound, heat and/or other standard methods. Then water is added to the mixture and gently mixed together using standard methods to receive a homogeneous transparent solution.

These formulations I, II, III and IV were stored at average room temperature, at 4° C. and at 35° C. Formulations I and IV were able to pass all temperatures. Formulation II, however, precipitated at 4° C. and formulation III became clouded at 35° C. Formulations I and IV were the only ones that were able to stay stable at all test-temperatures.

Example 6

Formulations were made to be used as nasal spray or ear drops to prevent and/or fight infections in the nose, the sinuses, ear canals, external ear etc. according to following:

| Component | Formulation | | | |
|---|---|---|---|---|
| | I | II | III | IV |
| Monocaprin | 0.25% | 0.25% | 0.25% | 0.25% |
| Monolaurin | 0.25% | 0.25% | 0.25% | 0.25% |
| mPEG* | 2% | 2% | — | 2% |
| Propylene glycol | 4% | 4% | 4% | 4% |
| Labrasol ™ | 10% | — | 10% | 10% |
| Ethanol | — | — | — | 2% |
| Polysorbate 80 | 0.8% | 0.8% | 0.8% | 0.8% |
| Water | 82.7% | 92.7% | 84.7% | 80.7% |

*Methoxypolyethylene glycol 350

Here the mPEG (formulation I, II and IV), propylene glycol, polysorbate 80, ethanol (formulation IV) and Labrasol™ (formulation I and III) are mixed together whereafter monocaprin and monolaurin (formulation I, II and III) are dissolved in this mixture using vortex, ultrasound, heat and/or other standard methods. Then water is added to the mixture and gently mixed together using standard methods to receive a homogeneous transparent solution.

These formulations I, II, III and IV were stored at ambient room temperature, at 4° C. and at 35° C. Formulations I and IV were able to pass all temperatures. Formulation II, however, precipitated at 4° C. and formulation III became clouded at 35° C. Formulations I and IV were the only ones that were able to stay stable at all test-temperatures.

Example 7

Formulations were made to be used as nasal spray or ear drops to prevent and/or fight infections in the nose, the sinuses, ear canals, external ear etc. according to following:

| Component | Formulation | | | |
|---|---|---|---|---|
| | I | II | III | IV |
| Monocaprin | 0.15% | 0.15% | 0.15% | 0.15% |
| Monolaurine | 0.35% | 0.35% | 0.35% | 0.35% |
| mPEG* | 2% | 2% | — | 2% |
| Propylene glycol | 4% | 4% | 4% | 4% |
| Labrasol ™ | 10% | — | 10% | 10% |
| Ethanol | — | — | — | 2% |
| Polysorbate 80 | 0.8% | 0.8% | 0.8% | 0.8% |
| Water | 82.7% | 92.7% | 84.7% | 82.7% |

*Methoxypolyethyelene glycol 350

Here the mPEG (formulation I, II and IV), propylene glycol, polysorbate 80, ethanol (formulation IV) and Labrasol™ (formulation I and III) are mixed together whereafter monocaprin and monolaurin (formulation I, II and III) are dissolved in this mixture using vortex, ultrasound, heat and/or other standard methods. Then water is added to the mixture and gently mixed together using standard methods to receive a homogeneous transparent solution.

These formulations I, II, III and IV were stored at average room temperature, at 4° C. and at 35° C. Formulations I and IV were able to pass all temperatures. Formulation II, however, precipitated at 4° C. and formulation III became clouded at 35° C. Formulation I and IV were the only ones that were able to stay stable at all test-temperatures.

Example 8

Formulations were made to be used as nasal spray or ear drops to prevent and/or fight infections in the nose, the sinuses, ear canals, external ear etc. according to following:

|  | Formulation | | | |
| --- | --- | --- | --- | --- |
| Component | I | II | III | IV |
| Monocaprin | 0.35% | 0.35% | 0.35% | 0.35% |
| Monolaurin | 0.15% | 0.15% | 0.15% | 0.15% |
| mPEG* | 2% | 2% | — | 2% |
| Propylene glycol | 4% | 4% | 4% | 4% |
| Labrasol ™ | 10% | — | 10% | 10% |
| Ethanol | — | — | — | 2% |
| Polysorbate 80 | 0.8% | 0.8% | 0.8% | 0.8% |
| Water | 82.7% | 92.7% | 84.7% | 80.7% |

*Methoxypolyethyelene glycol 350

Here the mPEG (formulation I, II and IV), propylene glycol, polysorbate 80, ethanol (formulation IV) and Labrasol™ (formulation I and III) are mixed together whereafter monocaprin and monolaurin (formulation I, II and III) are dissolved in this mixture using vortex, ultrasound, heat and/or other standard methods. Then water is added to the mixture and gently mixed together using standard methods to receive a homogeneous transparent solution.

These formulations I, IL, III and IV were stored at average room temperature, at 4° C. and at 35° C. Formulations I and IV were able to pass all temperatures. Formulation II, however, precipitated at 4° C. and formulation III became clouded at 35° C. Formulations I and IV were the only ones that were able to stay stable at all test-temperatures.

Example 9

Formulations were made that can be used as a nasal spray and eardrops, to prevent and/or fight infections in nose, sinuses, ear canals, external ear etc., according to Examples 1, 3, 5, 6, 7 and 8. However, instead of a mixture of monocaprin 0.5% and monolaurin 0.5%, there was monocaprin in 1% or monolaurine 1%.

These formulations I, II, III and IV were stored at average room temperature, at 4° C. and at 35° C. Formulations I and IV were thermostable and able to pass all temperatures. Formulation II, however, precipitated at 4° C. and formulation III became clouded at 35° C. Formulations I and IV were the only ones that were able to stay stable at all test-temperatures.

Example 10

Another thermostable formulation was manufactured that can be used as a nasal spray, eardrops, to prevent and/or fight infections in nose, sinuses, ear canals, external ear etc. The first one consisted of 1% monocaprin (40 mM) or 1% monolaurine, 50% methoxypolyethylene glycol 350, 30% propylene glycol and 20° A Labrasol™. The other consisted of 1% monocaprin (40 mM) or 1% monolaurin, 50% methoxypolyethylene glycol 350, 30% propylene glycol and 5% Softigen™ 767.

Exposing these formulations to storage temperatures of average room temperature, at 4° C. and at 35° C., both were found to be thermostable and able to pass all temperatures.

Example 11

Formulations were made that can be used as a nasal spray and eardrops, to prevent and/or fight infections in nose, sinuses, ear canals, external ear etc., according to Examples 1, 3, 5, 6, 7 and 8. However, instead of a mixture of polysorbate 80, there was polysorbate 20.

These formulations I, II, III and IV were stored at average room temperature, at 4° C. and at 35° C. Formulations I and IV (from Examples 1, 3, 5, 6, 7 and 8) were thermostable and able to pass all temperatures. Formulation II, however, precipitated at 4° C. and formulation III became clouded at 35° C. Formulations I and IV were the only ones that were able to stay stable at all test-temperatures.

Example 12

Formulation was manufactured for vaginal and/or rectal use, to prevent and/or fight infections in vaginal or rectal mucosa, consisting of 0.25 g of Monocaprin (1.6% or 20 mM) or 0.25 g of Monolaurin, 1 mL of Methoxypolyethylene glycol 350 (6.7%), 2 mL Labrasol™ or Softigen™ 767 and 10.5 g cocoa butter or adeps solidus.

During refrigeration, there is no precipitation of monocaprin or monolaurin, but it is evenly integrated with the remaining formulation.

Example 13

Formulation was manufactured for buccal, ocular or dermal delivery that can be used to fight infections in the eyes, in the mouth or on the skin. The formulation consisted of monocaprin in 0.5% (20 mM) concentration or monolaurin in 0,5% concentration or combination thereof, 10% methoxypolyethylene glycol 350, 5% of propylene glycol, from 1-10% of Labrasol™ or Softigen™ 767, 0.8% of polysorbate 80 and water.

Example 14

Formulation was manufactured for buccal, ocular or dermal delivery that can be used to fight infections in eyes, in mouth or the skin. The formulation consisted of monocaprin in 0.5% (20 mM) concentration or monolaurin in 0,5% concentration or combination thereof, 10% methoxypolyethylene glycol 350, 5% of propylene glycol, from 1-10% of Labrasol™ or Softigen™ 767, 0.8% of polysorbate 80, traces of HPMC and water.

Example 15

Formulation was manufactured as described in Examples 1, 3, 5, 6, 7 and 8, that also contain spermicides as surfactants such as nonoxynol-9, chelating agents such as ethylenediaminetetraacetic acid (EDTA), that may be used to deliver the formulation to the nasal cavity, sinuses, ear, oral cavity, pharynx, larynx, vagina, rectum, eye and the skin.

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components.

The present invention also covers the exact terms, features, values and ranges etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

It will be appreciated that variations to the foregoing embodiments of the invention can be made while still falling within the scope of the invention can be made while still falling within scope of the invention. Features disclosed in the specification, unless stated otherwise, can be replaced by alternative features serving the same, equivalent or similar purpose. Thus, unless stated otherwise, each feature disclosed represents one example of a generic series of equivalent or similar features.

Use of exemplary language, such as "for instance", "such as", "for example" and the like, is merely intended to better illustrate the invention and does not indicate a limitation on the scope of the invention unless so claimed. Any steps described in the specification may be performed in any order or simultaneously, unless the context clearly indicates otherwise.

The invention claimed is:

1. A pharmaceutical formulation for antimicrobial treatment through application to skin or mucosa, comprising:
   a. an antimicrobiologically active lipid selected from the group consisting of glycerol monocaprate, glycerol monocaprylate,-glycerol monolaurate, propylene glycol monocaprate, propylene glycol monocaprylate, propylene glycol monolaurate, glycerol dicaprin, glycerol dicaprylate, glycerol dilaurate, glycerol tricaprin, glycerol tricaprylate, glycerol trilaurate, octylglycerol, monomyristin, monopalmitolein, monoolein, propylene glycol monocaprylate, propylene glycol monolaurate, and any combination thereof, in a concentration in the range from about 0.01 to about 5 wt %,
   b. one or more methoxypolyethylene glycol represented by the formula I:

CH$_3$—(O—CH$_2$—CH$_2$)$_n$—H          (I)

wherein n is an integer in the range from 1 to 25, in an amount in the range from about 0.1 to about 60 wt %, and
   c. one or more polyoxyethylene-glyceride in an amount in the range from about 0.1 to about 60% having the formula (II):

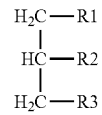

wherein R1, R2, and R3 are independently selected from the group consisting of C$_6$ to C$_{22}$ fatty acids, polyoxyethylene glycol (PEG), and hydrogen, provided that it contains at least one C$_6$-C$_{22}$ fatty acid and at least one PEG group.

2. The formulation according to claim 1, wherein said methoxypolyethylene glycol comprises mPEG350 and/or mPEG550.

3. The formulation according to claim 1, wherein in said one or more polyoxyethylene glycol-fatty acid glyceride, one of R1, R2 and R3 comprises a C$_6$-C$_{22}$ fatty acid, and the remaining two R-groups comprise polyoxyethylene glycol, or two of R1, R2 and R3 comprise C$_6$-C$_{22}$ fatty acid, and the remaining R-group comprises polyoxyethylene glycol.

4. The formulation according to claim 1, wherein said antimicrobiologically active lipid is in a concentration in the range from about 0.1 to about 2 wt %.

5. The formulation according to claim 1, wherein said methoxypolyethylene glycol is in a concentration in the range from 0.2 wt % to 20 wt %.

6. The formulation according to claim 1, wherein said polyoxyethylene-glyceride is in a concentration in the range from 0.2 wt % to 20 wt %.

7. The formulation according to claim 1, wherein said polyoxyethylene-glyceride comprises one or more substance selected from caprylcaproyl polyoxyl-8 glycerides.

8. The formulation according to claim 1, provided in a dosage unit having a formulation volume of 10 mL or less.

9. The formulation according to claim 1, further comprising ethanol in a concentration in the range from about 0.2 wt % to about 3 wt %.

10. The formulation according to claim 1, formulated in a form selected from the group consisting of spray, aerosol, mist, drops, creme, gel, suppository, vagitory, solution and ointment.

11. The formulation according to claim 1, further comprising a substance selected from polyethylene glycol, a buffer, a spermicide, and a chelating agent.

12. The formulation according to claim 1, wherein said antimicrobiologically active lipid is in a concentration in the range from about 0.1 to about 1 wt %.

13. The formulation according to claim 1, wherein said methoxypolyethylene glycol is in a concentration in the range from 0.5 to 5 wt %.

14. The formulation according to claim 1, wherein said polyoxyethylene-glyceride is in a concentration in the range from 0.5 to 10 wt %.

15. The formulation according to claim 1, provided in a dosage form having a formulation volume of 1.0 mL or less.

16. The formulation according to claim 1, provided in a dosage form having a formulation volume of 0.5 mL or less.

17. The formulation according to claim 1, provided in a dosage form having a formulation volume within the range from about 50 μL to about 300 μL.